United States Patent [19]

Markhart et al.

[11] 3,991,253

[45] *Nov. 9, 1976

[54] DIELECTRIC RECORDING MEDIA

[75] Inventors: Albert H. Markhart; David R. Cahill, both of Wilbraham, Mass.

[73] Assignee: Monsanto Company, St. Louis, Mo.

[ * ] Notice: The portion of the term of this patent subsequent to Apr. 20, 1993, has been disclaimed.

[22] Filed: Jan. 27, 1975

[21] Appl. No.: 544,100

Related U.S. Application Data

[63] Continuation of Ser. No. 339,450, March 8, 1973, abandoned.

[52] U.S. Cl. .......................... 428/325; 260/33.4 R; 260/33.6 UA; 252/63.5; 428/323; 428/328; 428/334; 428/336; 428/404; 428/407; 428/461; 428/463; 428/537; 428/511; 428/514; 428/526
[51] Int. Cl.² ...................... B32B 5/16; H01B 3/02
[58] Field of Search............... 117/201, 218, 221; 106/308, 300, 299; 428/336, 334, 325, 328, 407, 404, 460, 461, 463, 507, 514, 526, 511, 537, 323; 427/58, 215, 218, 220; 260/33.4 R, 33.6 UA, 41 A; 252/63.5

[56] References Cited
UNITED STATES PATENTS

| | | | |
|---|---|---|---|
| 2,621,193 | 12/1952 | Langkammerer | 260/414 |
| 3,032,431 | 5/1962 | Ferrigno | 106/308 Q |
| 3,293,115 | 12/1966 | Lucken | 117/201 |
| 3,582,378 | 6/1971 | Miller | 106/308 Q |
| 3,639,162 | 1/1972 | Bixler | 117/201 |
| 3,653,894 | 4/1972 | Levy | 117/201 |
| 3,660,134 | 5/1972 | Morris | 106/300 |
| 3,694,202 | 9/1972 | Sawyer | 117/201 |
| 3,697,474 | 10/1972 | Morris | 106/308 Q |
| 3,697,475 | 10/1972 | Morris | 106/308 Q |
| 3,708,289 | 1/1973 | Timmerman | 117/201 |
| 3,951,882 | 4/1976 | Markhart | 252/63.5 |

*Primary Examiner*—George F. Lesmes
*Assistant Examiner*—Ellis P. Robinson
*Attorney, Agent, or Firm*—R. Bruce Blance; James C. Logomasini

[57] ABSTRACT

A dielectric recording medium comprising an electroconductive substrate and a coating of dielectric resin binder in which there is dispersed an organophilic clay pigment. The organophilic clay pigment comprises a kaolin clay treated with an organotitanium compound. The pigment imparts a bond appearance to the dielectric recording medium and enhances the tooth or ease of marking of the coating with ink.

13 Claims, No Drawings

DIELECTRIC RECORDING MEDIA

This is a continuation, of application Ser. No. 339,450, filed Mar. 8, 1973, now abandoned.

BACKGROUND OF THE INVENTION

1. Field of the Invention

This invention relates to dielectric recording media which are used in electrostatographic printing processes and to methods of making such media. In another aspect, it relates to dielectric resin coating compositions.

2. Description of the Prior Art

In electrostatographic printing processes an electrostatic charge pattern is applied to the recording medium directly or by a transfer technique and is developed by any of the conventional toning techniques to form a permanent visible image. The dielectric recording medium should accept an electrostatic charge rapidly and retain it sufficiently long for the charge pattern to be developed. A number of dielectric recording media have been described in the prior art.

Typical dielectric recording media comprise an electro-conductive substrate and a coating of dielectric resin. While they have, in general, been adequate in their dielectric properties and electrostatic charge acceptance, they have been deficient in appearance and feel because the dielectric coatings present surfaces of high gloss and smoothness. Moreover, such surfaces are unsatisfactory because of lack of "tooth" or receptivity to marking by conventional means such as pencil, pen and ink, etc.

Incorporation of pigments into the dielectric coatings can overcome these deficiencies of appearance and lack of tooth but usually with a sacrifice in electrical properties. For example, clay pigments which are widely used in paper coatings, have been found to inhibit drastically the ability of a coating to accept and hold an electrostatic charge. Other common pigments exhibit similar unsatisfactory behavior.

Thus, there exists in the art a need for a dielectric recording medium comprising a dielectric coating containing a low-cost pigment and possessing adequate electrical and physical properties.

SUMMARY OF THE INVENTION

The above-mentioned need in the art is fulfilled by the present invention which provides pigmented dielectric coating compositions comprising a dispersion in an organic solvent of a dielectric resin binder and a finely divided calcined kaolin clay which has been rendered organophilic by surface treatment with an organotitanium compound of the formula:

wherein R is a hydrocarbon radical containing from 1 to 12 carbon atoms, and R' may be OCOR'' or OR''' or a hydrocarbon substituted silicic acid radical (O Si R''), wherein R'' is a substituted or unsubstituted hydrocarbon radical having from 1 to 40 carbon atoms and wherein R''' is a substituted or unsubstituted hydrocarbon radical having from 6 to 40 carbon atoms and wherein R''' is not identical to R, and wherein m is equal to 2 or 3.

The invention further provides pigmented dielectric coatings comprising a dielectric resin binder and the above-described treated kaolin clay and dielectric recording media comprising electro-conductive substrates coated with the pigmented dielectric coatings comprising a dielectric resin binder and the above-described treated kaolin clay, such dielectric recording media being characterized by their non-glossy surfaces, receptiveness to marking by ink, and by their ability to accept and retain an electrostatic charge particularly under conditions of high humidity.

The invention further provides a method of making dielectric recording media which possess the feel and appearance of bond paper, are readily marked by ink, and accept and retain an electrostatic charge particularly under conditions of high humidity, which comprises dispersing an organophilic clay pigment in a dielectric resin binder and applying the dispersion to an electroconductive substrate to provide a dielectric layer on the substrate.

DESCRIPTION OF THE PREFERRED EMBODIMENTS

The pigmented dielectric coating compositions of the present invention are prepared by blending a dielectric resin with an organophilic kaolin clay.

The dielectric resin functions as an insulating medium when it is coated on an electroconductive substrate, thus providing the charge accepting surface of the composite dielectric recording medium. The resin is a substantially hydrophobic resin with adhesive affinity for the substrate and for the organophilic calcined kaolin clay. A great variety of organic resins meet these requirements including addition polymers containing at least one monomer selected from the group consisting of vinyl esters, vinyl acetals, vinyl halides, vinylidene halides, alkyl acrylates, alkyl methacrylates, alkyl maleates, alkyl fumarates, olefins, dienes, vinylidene aromatic hydrocarbons, and $\alpha,\beta$-ethylenically unsaturated nitriles; cellulosics such as cellulose acetate, cellulose butyrate and methyl and ethyl cellulose; condensation polymers such as polyesters, polycarbonates, alkyds, polyurethanes, polyimides, polysulfones and silicones, and the like. The addition polymers may optionally be modified with minor amounts of acid or hydroxyl comonomers.

The preferred resins include poly(vinyl acetals) such as poly(vinyl formals) and poly(vinyl butyrals) and interpolymers of styrene and substituted styrenes with alkyl acrylates or alkyl methacrylates. The poly(vinyl butyral) resins are characterized by a vinyl acetate content of less than 10 per cent by weight, a vinyl alcohol content of from 9 to 21 per cent by weight and a weight average molecular weight in the range of 20,000 to 500,000. Particularly preferred poly(vinyl butyrals) have a "vinyl alcohol" content of from 9 to 13 per cent.

The interpolymers of styrene or a substituted styrene containing 9–13 carbon atoms and an acrylic or methacrylic ester of a $C_1$ to $C_8$ saturated monohydric aliphatic alcohol comprise from 30 to 70 parts by weight of styrene or substituted styrene and 30 to 70 parts by weight of acrylic or methacrylic ester and optionally up to 10 parts by weight of an acid comonomer such as acrylic acid, methacrylic acid, crotonic acid or maleic acid, the relative viscosity of the interpolymer being in the range of 1.1 to 3.0 when measured as a 2 per cent solution in benzene.

The organophilic kaolin clays are prepared from calcined kaolin clay with a water content in the range of 0.1 to 2 weight per cent by treating the surface with a specific class of organotitanium compounds. The preferred clays are those of particle size in the range of 0.1 to 20 micron. Treatment of the clay is carried out by adding a dilute solution of organotitanium compound in an inert anhydrous solvent to a slurry of the clay in the inert anhydrous solvent and stirring the slurry until reaction is complete. Solvent and hydrolysis products are removed by distillation or filtration. The amount of organotitanium compound used will vary from about 0.5 to about 6 weight per cent based on the dry weight of the inorganic material.

The organotitanium compounds used to react with the inorganic filler material is represented by the formula $Ti(OR)_m R'_{4-m}$ wherein R is a hydrocarbon radical containing from 1 to 12 carbon atoms and R' may be OCOR'', OR''', or a hydrocarbon substituted silicic acid radical (OSiR'') wherein R'' is a substituted or unsubstituted hydrocarbon radical having from 1 to 40 carbon atoms and wherein R''' is a substituted or unsubstituted hydrocarbon radical having from 6 to 40 carbon atoms providing that R''' and R are not identical. In the formula m is equal to 2 or 3. At least two hydrolyzable groups, preferably OR groups, must be present in the organotitanium compound.

The organotitanium compound is prepared by reacting 1 mol of $Ti(OR)_4$ with from 1 to 2 mols of a compound represented by the formula AR' wherein A is a hydrogen or a group capable of reacting to remove an OR from the $Ti(OR)_4$ molecule and R' is as described above. A mixture of two or more compounds of the formula AR' may be used. The preparation of illustrative organotitanium compounds is more particularly described in U.S. Pat. No. 2,621,193.

Referring to the starting material $Ti(OR)_4$, R is selected from the group consisting of alkyl, cycloalkyl, aryl, aralkyl, and alkaryl radicals containing from 1 to 12 carbon atoms. Specific examples of compounds represented by the formula are tetramethyl titanate, tetraethyl titanate (ethyl orthotitanate), tetrabutyl, tetraisopropyl, tetraamyl, tetraoctyl, tetradodecyl, tetra-2-ethyl-hexyl, tetrabenzyl, tetraphenyl and tetrabetanaphthyl titanates.

The radical R'' mentioned above represents a hydrocarbon radical having from 1 to 40 carbon atoms taken from the group consisting of alkyl, cycloalkyl, aryl, aralkyl, alkaryl hydrocarbon radicals which may contain various substituents such as halogens, e.g., a perfluoro methyl radical, hydroxyl group, keto group (radical of levulinic acid) amino, nitro and heterocyclic groups. Examples of R'' groups are methyl, ethyl, propyl, butyl, pentyl, hexyl, heptyl, octyl, octadecyl, cyclohexyl, cycloheptyl, phenyl, naphthyl, tolyl, xylyl, benzyl, phenyl ethyl, chlorophenyl, dibromophenyl, 2,3-dihydroxy propoxy. The various hydrocarbon radicals may contain aliphatic unsaturation as well as aromatic unsaturation. Perfluoro compounds may be used. R''' is of similar scope but with the exclusion of radicals containing 5 or less carbon atoms.

A preferred class of compounds represented by the formula AR' are the organic aromatic and aliphatic carboxylic acids. The resulting organotitanium compound may be called an ester carboxylate or an ester anhydride of ortho titanic acid. Among the aliphatic and aromatic organic acids that may be used are straight or branch chain, saturated or unsaturated, substituted or unsubstituted mono- or poly-carboxylic acids including such acids as stearic, palmitic, ricinoleic, linoleic, lauric, myristic, oleic, benzoic, caproic, caprylic, nonylic, capric, linseed oil acids, castor oil acids, tall oil acids, cocoanut oil acids, soybean oil acids, tung oil acids, perfluorooctanoic acid, phthalic acid, adipic acid, etc.

A second class of useful compounds which generally will be used in conjunction with one of the acids cited above, although they can be used as sole component of the reaction with the $Ti(OR)_4$ are the organic alcohols or organic phenols. Among such compounds are 2-phenoxyethanol, m-cresol, diethylene glycol, 2,6-dioctadecyl cresol, 1-(2-pyridylazo)-2-naphthol, naphthol, anisyl alcohol, glycerol, geraniol, etc.

In some cases, the combined effect of the two classes just cited may be obtained by using an ester as the triglyceride of ricinoleic acid.

The preparation of typical organotitanium compounds and their application to calcined clay is described more fully in U.S. Pat. No. 3,660,134.

Especially preferred organotitanium compounds for the reaction with kaolin clay include trialkyl oleyl titanates and dialkyl dioleyl titanates wherein the alkyl group contains 2–8 carbon atoms such as ethyl, propyl, isopropyl, n-butyl, 2-ethylhexyl, n-octyl and the like.

The electroconductive substrate can be a metal foil, or a non-metallic cellulosic or synthetic sheet or paper coated on one or both sides to make it electrically conductive. Conductivity corresponding to a surface resistivity less than $1 \times 10^9$ ohms per square at 50 per cent relative humidity is adequate. Such conductivity can be imparted to the non-metallic sheet by applying a thin metallic film or a coating containing inorganic salts or an electroconductive resin such as poly(vinylbenzyl trimethylammonium chloride) or poly(diallyl dimethylammonium chloride) and the like.

Dispersions of the dielectric resin and the organophilic calcined kaolin clay can be prepared by dissolving the dielectric resin in an organic solvent and stirring the treated clay into the solution by conventional means to give a smooth dispersion which is then applied to the electroconductive substrate by conventional coating techniques and dried to yield a dielectric recording medium. Solvents suitable for such dispersions include aromatic solvents such as benzene, toluene, xylenes; petroleum naphtha, chlorinated solvents such as trichloroethylene, alcohols, esters, ketones, etc. The solvent which is selected for the dispersion should be a non-solvent for the substrate and for the electroconductive component of the substrate. When the dielectric resin is a styrene copolymer, the preferred solvent is an aromatic hydrocarbon containing 6 to 9 carbon atoms such as benzene, toluene or a xylene. When the dielectric resin is a poly(vinyl butyral), the preferred solvent is a blend of an aromatic hydrocarbon containing 6 to 9 carbon atoms such as benzene, toluene, or a xylene and a lower alcohol containing 1 to 4 carbon atoms such as methanol, ethanol, n-propyl alcohol or n-butyl alcohol, the weight ratio of aromatic hydrocarbon to alcohol being in the range of 80:20 and 20:80.

The solids content of the solvent dispersion can be in the range of 10 to 70 per cent by weight and is selected to give a viscosity in the range of 50 to 10,000 cps. for ease of coating with conventional coating equipment.

Treatment of the clay and formation of the coating dispersion can be combined in a process wherein organotitanium compound is dissolved in an anhydrous inert solvent, the resulting solution is added to the calcined kaolin clay and stirred until reaction is complete and a second solution of dielectric resin in the inert anhydrous solvent is added and stirred until a uniform dispersion is obtained.

Dispersions of dielectric resin and organophilic calcined kaolin clay can be prepared by heat working of the clay and resin at a suitable temperature above the softening point of the resin. The dispersion can then be applied by hot melt extrusion techniques to an electroconductive substrate to yield a dielectric recording medium.

The weight ratio of dielectric resin to organophilic kaolin clay is between 7:3 and 1:8. With a ratio above 7:3, little influence on the surface gloss and tooth of the dielectric coating is obtained. With a ratio below 1:8, the ability of the surface to accept and retain a charge is excessively impaired. The preferred weight ratio is in the range of 4.5:5.5 and 2.5:7.5 since in this range a bond-like appearance and ease of marking with a ball-point pen are obtained and the dielectric coatings are superior in charge acceptance to coatings with conventional pigments especially under conditions of high humidity.

The thickness of the dielectric coating can be varied in the range of from 0.03 to 5 mil. However, in dielectric recording media for direct electrography, a coating of from 0.05 to 0.3 mil is preferred and in dielectric recording media for use in transfer electrography a dielectric coating of from 0.3 to 1.0 mil is preferred.

The following examples are set forth in illustration of the present invention and should not be construed as a limitation thereof. Unless otherwise indicated, all parts and percentages are by weight.

EXAMPLE 1

PREPARATIN OF A DIELECTRIC COATING COMPOSITION AND DIELECTRIC RECORDING MEDIA

Diisopropyl dioleyl titanate is prepared by mixing 2.14 parts by weight of tetraisopropyl titanate with 4.28 parts by weight of oleic acid at room temperature, stirring the mixture which becomes warm on mixing and allowing the mixture to cool to room temperature. The product diisopropyl dioleyl titanate is dissolved in 600 parts by weight of trichloroethylene and 430 parts by weight of calcined clay containing about 0.4 per cent adsorbed water is slowly added over a period of 15 minutes accompanied by constant stirring. The slurry is stirred for a further 30 minutes. The solvent is evaporated and the dry product which contains about 1.5 per cent by weight of organotitanate is micropulverized to a product with 70 per cent of average particle size less than 2 microns.

Fifty parts by weight of a poly(vinyl butyral) characterized by a vinyl acetate content of 1.5 per cent, a hydroxyl content of 12.0 per cent and a weight average molecular weight of 50,000 are dissolved in a solvent blend containing 240 parts by weight of toluene and 160 parts by weight of ethanol. The solution is added to an explosion-proof Waring Blender. Fifty parts by weight of the treated clay product are added to the slowly stirred solution. Stirring is then carried out for 2 minutes at high speed and a smooth uniformly dispersed coating composition is obtained.

The coating composition is coated on an electroconductive paper of surface resistivity $10^{-8}$ ohms per square at 50 per cent relative humidity and a basis weight of 40 pounds per 3000 sq. ft. by means of wire wound rods selected to give coating weights in the range of from two to seven pounds per 3000 sq. ft. Thus, dielectric recording media with various thicknesses of dielectric coating are obtained. The dielectric surfaces of the media have the feel and appearance of bond paper and are receptive to marking by pencil, pen and ink, ball-point pen and the like.

EVALUATION OF DIELECTRIC RECORDING MEDIA

The dielectric recording media are evaluated by determination of their ability to accept and retain an electrostatic charge at 50 per cent relative humidity. A test instrument sold under the trademark STATI-TESTER by Most Associates is used in the determination. A negative charge is applied by the corona source at a constant current of 40 microamperes, until the maximum surface voltage is reached. This maximum voltage is designated the initial voltage. The ability to retain the charge is assessed from the voltage decay over a 60 second period.

The data for various coating weights are presented in Table 1.

TABLE 1

| Coating Weight Lbs. per 3000 sq.ft. | Initial Voltage | Voltage After 60 Sec. |
|---|---|---|
| 2.4 | 237 | 97 |
| 4.0 | 360 | 110 |
| 5.4 | 415 | 130 |
| 7.4 | 560 | 200 |

A charge pattern is generated on the dielectric recording medium comprising the dielectric coating of 5.4 pounds per 3000 sq. ft. by passing the dielectric recording medium under a pulsed stylus at a rate of 300 inches per second. The stylus is operated at a potential of 600 volts negative and with a 25 microsecond pulse. The charge pattern is developed by applying a positively charged toner over the surface. The developed image is set by exposing the dielectric recording medium to heat to fuse the toner particles and provide a permanent visible image on the dielectric recording medium. In this fashion, a print on the dielectric recording medium is obtained.

EXAMPLE 2

This example is set forth to show the preparation of the dielectric coating composition without the intermediate separation of the organophilic clay from the reaction slurry.

A slurry of 50 parts by weight of calcined clay of 1 per cent water content, in 100 parts by weight of toluene is prepared in a Waring Blender, and treated with 0.75 parts of diisopropyl dioleyl titanate in 20 parts of toluene by slowly adding the titanate solution to the clay dispersion.

A solution of 50 parts by weight of the poly(vinyl butyral) of Example 1 in 120 parts by weight of toluene and 160 parts by weight of ethanol is added to the slowly stirred slurry. The slurry is then stirred at high speed for 2 minutes to yield a smooth uniformly dispersed coating composition.

The coating composition is coated on electroconductive paper in the manner described in Example 1. A dielectric recording medium comprising a dielectric coating of 5 pounds per 3000 sq. ft. accepts a surface charge of more than 350 volts.

EXAMPLES 3–6

These examples are set foth to illustrate the preparation of dispersions of dielectric coating compositions from a variety of organophilic clays. The procedure of Example 1 is followed using finely divided calcined delaminated clay heated with various organotitanium compounds. The dielectric resin is the poly(vinyl butyral) of Example 1. The compositions are set forth in Table 2.

TABLE 2

DISPERSIONS OF DIELECTRIC COATING COMPOSITIONS, PARTS BY WEIGHT

| Ex. | Clay | Organophilic Treatment | Poly(vinyl butyral) | Solvent Toluene | Solvent Ethanol |
| --- | --- | --- | --- | --- | --- |
| 3 | 50 | triisopropyl monooleyl titanate, 0.5 parts | 50 | 240 | 160 |
| 4 | 50 | bis-(2-ethylhexyl) dioleyl titanate 1.5 parts | 50 | 160 | 240 |
| 5 | 50 | diisopropyl dilauroyl titanate, 0.5 parts | 50 | 240 | 160 |
| 6 | 50 | bis-(2-ethylhexyl) dicapryl titanate 0.5 parts | 50 | 240 | 160 |

Dielectric recording media prepared from these dispersions and comprising coatings of 5 pounds per 3000 sq. ft. are evaluated on the Most "Stati-tester". They show an initial charge acceptance of more than 300 volts. They have a bond-like feel and readily accept marking by pencil, pen and ink, ball-point pen and the like.

EXAMPLE 7

This example is set forth to demonstrate the effect of variation in the ratio of pigment to dielectric binder on the performance of the dielectric recording medium.

A series of dispersions containing various ratios of pigment to binder is prepared using the pigment, binder and procedure of Example 1. The dispersions are coated onto the electroconductive paper of Example 1 at various coating weights. The dielectric recording media are evaluated on the Most Stati-tester. The data for each pigment to binder ratio are normalized to a coating weight of 5.0 pounds per 3000 sq. ft. The data are presented in Table 3. Included in the Table are data for appearance and mark acceptance which is determined by the ease of marking with a ball-point pen.

TABLE 3

| Pigment: Binder Weight Ratio | Initial Voltage, Volts (normalized 5 lb. coating wt.) | Appearance | Mark Acceptance |
| --- | --- | --- | --- |
| 10:90 | 650 | glossy | poor |
| 30:70 | 540 | slightly glossy | fair |
| 50:50 | 490 | matte | good |
| 70:30 | 220 | bond-like | excellent |

EXAMPLE 8

This example is set forth to demonstrate the superiority of the organophilic clay pigment of Example 1 to a variety of conventional pigments. In each case, the dielectric resin binder of Example 1 is used. A series of dispersions containing various ratios of pigment to binder is prepared for each pigment. The dispersions are coated on the electroconductive paper of Example 1 at various coating weights. The dielectric recording media thus obtained are evaluated on the Most Stati-tester. The data, normalized to a coating weight of 5.0 pounds per 3000 sq. ft., are presented in Table 4.

TABLE 4

| Dielectric Recording Medium | Initial Voltage, Volts, 5 lb. coating weight | | | |
| --- | --- | --- | --- | --- |
| Pigment:binder (wt. ratio) | 10:90 | 30:70 | 50:50 | 70:30 |
| Treated clay (Ex. 7) | 650 | 540 | 390 | 220 |
| Lithopone 40M | 560 | 460 | 350 | 240 |
| Titanium dioxide | 580 | 430 | 240 | 110 |
| Barium sulfate | 480 | 350 | 250 | 150 |
| Calcium carbonate | 360 | 190 | 85 | 40 |
| Clay | 440 | 120 | 40 | 20 |

The data show that the ability to accept a charge declines with increase in the pigment to binder ratio of the series of dielectric recording media. However, the recording media containing the organophilic clay pigment are generally superior to media containing conventional pigments.

EXAMPLE 9

This example is set forth to demonstrate the superiority of the organophilic clay pigment of Example 1 to a variety of conventional pigments which have been subjected to treatment with diisopropyl dioleyl titanate, the organophilicizing agent of Example 1.

Samples of lithopone 40M, titanium dioxide and barium sulfate pigments are treated with diisopropyl dioleyl titanate in the fashion described for calcined clay in Example 1. The treated pigments are then formulated in a series of dispersions containing various ratios of pigment to binder. Dielectric recording media are prepared from the dispersions by the procedure of Example 1. They are evaluated on the Most Stati-tester.

TABLE 5

| Dielectric Recording Medium | Initial Voltage Volts, 5 lb. coating weight | | | |
| --- | --- | --- | --- | --- |
| Pigment:binder (wt. ratio) | 10:90 | 30:70 | 50:50 | 70:30 |
| Clay | 440 | 120 | 40 | 20 |
| Treated clay (Ex. 7) | 650 | 540 | 390 | 220 |
| Lithopone 40M | 560 | 460 | 350 | 240 |
| Treated Lithopone 40M | 630 | 450 | 290 | 160 |
| Titanium dioxide | 580 | 430 | 240 | 110 |
| Treated titanium dioxide | 530 | 250 | 70 | 10 |
| Barium sulfate | 480 | 350 | 250 | 150 |
| Treated barium sulfate | 570 | 300 | 130 | 60 |

The data show the improvement in dielectric properties of clay pigmented coatings, achieved by treatment of clay with the organotitanium compounds of Example 1 in contrast to the decline in dielectric properties of the other pigmented coatings in which the pigment has been similarly treated with organotitanium compound. The contrast is particularly marked at pigment loadings of 50 per cent or more.

EXAMPLE 10

This example is set forth to show the superiority of the organophilic clay pigment of Example 1 in dielectric recording media under conditions of high humidity.

The dielectric recording media of Example 7 are evaluated on the Most Stati-Tester at 80 per cent relative humidity. Similarly, the Lithopone dielectric recording media of Example 8 are evaluated at this humidity. The data, normalized to a coating weight of 5.0 pounds per 3000 sq. ft., are presented in Table 6 in comparison with the data obtained at the standard relative humidity of 50 per cent.

TABLE 6

| Dielectric Recording Medium | Initial Voltage, Volts, 5 lb. coating weight | | | |
|---|---|---|---|---|
| Pigment:binder (wt. ratio) | 10:90 | 30:70 | 50:50 | 70:30 |
| Treated clay (Ex. 7) | | | | |
| 50% R.H. | 650 | 540 | 390 | 220 |
| 80% R.H. | 350 | 230 | 170 | 120 |
| Lithopone 40M | | | | |
| 50% R.H. | 560 | 460 | 350 | 240 |
| 80% R.H. | 490 | 230 | 130 | 40 |

The data show the expected fall in charge acceptance at the higher relative humidity. However, at high pigment loading of the dielectric layer, the dielectric recording media containing organophilic clay pigment are much less susceptible to humidity than the recording media containing Lithopone.

EXAMPLE 11

This example is set forth to illustrate a styrene-ethyl acrylate interpolymer as the dielectric resin binder.

The interpolymer is prepared by conventional free radical solution polymerization technique from a monomer mixture of 47 parts by weight styrene, 50 parts by weight ethyl acrylate, and 3 parts by weight methacrylic acid in toluene. The relative viscosity of a 2 per cent solution of the interpolymer in benzene is 1.50. The solution interpolymer contains 50 weight per cent solids.

A series of dispersions containing various pigment to binder ratios is prepared by the procedure of Example 1, using the interpolymer, the organophilic clay pigment of Example 1, and toluene as the solvent.

Each dispersion is coated on the electroconductive paper of Example 1 at various coating weights to yield a series of dielectric recording media. The media are evaluated on a Most Stati-Recorder at 50% relative humidity. The data, normalized to a coating weight of 5.0 pounds per 3000 sq. ft., are presented in Table 7.

TABLE 7

| Pigment:binder (wt. ratio) | Initial Voltage, volts 5 lb. coating wt. |
|---|---|
| 10:90 | 580 |
| 30:70 | 560 |
| 50:50 | 340 |
| 70:30 | 170 |

EXAMPLE 12

This example is set forth to illustrate a t-butylstyrene ethyl acrylate interpolymer as the dielectric resin binder.

The interpolymer is prepared by free radical solution polymerization technique from a monomer mixture of 47 parts by weight t-butylstyrene, 50 parts by weight ethyl acrylate, and 3 parts by weight acrylic acid in a blend of 67 parts by weight toluene and 33 parts by weight xylene. The relative viscosity of a 2 per cent solution of the interpolymer in benzene is 1.55.

The binder is evaluated in dielectric coatings containing the organophilic clay pigment of Example 1 by the procedure set forth in Example 11. The data are presented in Table 8.

TABLE 8

| Pigment:binder (wt. ratio) | Initial Voltage, volts 5 lb. coating wt. |
|---|---|
| 10:90 | 620 |
| 30:70 | 590 |
| 50:50 | 370 |
| 70:30 | 190 |

It will be obvious that many variations can be made to the products and processes of this invention. Conventional additives such as plasticizers, adhesion promoters, wetting agents, flow control additives and viscosity modifiers may be added to the dielectric coating compositions without departing from the scope of the invention.

What is claimed is:

1. A dielectric recording medium which comprises an electroconductive substrate coated on at least one surface with a dielectric coating of thickness in the range of from 0.03 to 5 mil, said coating comprising a dielectric resin binder and an organophilic clay pigment dispersed therein; wherein the weight ratio of dielectric resin binder to organophilic clay pigment is in the range of 7:3 to 1:8, wherein the dielectric resin binder is a poly(vinyl butyral) containing from 9 to 21 weight percent "vinyl alcohol" and less than 10 weight percent vinyl acetate and is of weight average molecular weight in the range of 20,000 to 500,000; and wherein the organophilic clay pigment is the reaction product of calcined kaolin clay of particle size in the range of 0.1 to 20 micron containing from 0.1 to 2 percent by weight of water and from about 0.5 to about 6 percent by weight of an organotitanium compound containing at least two hydrolyzable groups, the organotitanium compound being represented by the formula:

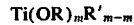

$$Ti(OR)_m R'_{m-m}$$

wherein R is a hydrocarbon radical containing from 1 to 12 carbon atoms and R' is OCOR'', OR''', or OSiR'', wherein R'' is a substituted or unsubstituted hydrocarbon radical having from 1 to 40 carbon atoms and wherein R''' is a substituted or unsubstituted hydrocarbon radical having from 6 to 40 carbon atoms providing that R''' and R are not identical and wherein m is an integer of 2 or 3.

2. The dielectric recording medium of claim 1 wherein R is a hydrocarbon radical containing 1 to 8 carbon atoms and R' is a carboxyl group containing 1 to 40 carbon atoms.

3. The dielectric recording medium of claim 1 wherein the weight ratio of dielectric resin binder to organophilic clay pigment is in the range of 4.5:5.5 to 2.5:7.5.

4. The dielectric recording medium of claim 1 wherein the electroconductive substrate is a paper sheet with basis weight in the range of 15 to 100 pounds per 3000 sq. ft. and a surface resistivity less than 1 × 10$^9$ ohms per square at 50 per cent relative humidity.

5. The dielectric recording medium of claim 1 wherein the thickness of the dielectric coating is in the range of 0.03 to 1.0 mil.

6. The dielectric recording medium of claim 1 wherein the "vinyl alcohol" content of the polyvinyl butyral is between 9 and 13 weight per cent and the vinyl acetate content is between 0 and 2.5 weight per cent.

7. A dielectric recording medium which comprises an electroconductive substrate coated on at least one surface with a dielectric coating of thickness in the range of from 0.03 to 5 mil, said coating comprising a dielectric resin binder and an organophilic clay pigment dispersed therein; wherein the organophilic clay pigment is the reaction product of calcined clay of particle size in the range of 0.1 to 20 micron containing from 0.1 to 2 percent by weight of water and from about 0.5 to about 6 percent by weight of an organotitanium compound selected from the group consisting of trialkyl monooleyl titanate and dialkyl dioleyl titanate, wherein the alkyl group contains 1 to 8 carbon atoms; wherein the dielectric resin is a polyvinyl butyral of weight average molecular weight in the range of 20,000 to 500,000 containing from 9 to 21 weight percent "vinyl alcohol" and less than 10 weight percent vinyl acetate; and wherein the weight ratio of dielectric resin binder to organophilic clay pigment is in the range of 7:3 to 1:8.

8. A dielectric recording medium which comprises an electroconductive substrate coated on at least one surface with a dielectric coating of thickness in the range of from 0.03 to 5 mil, said coating comprising a dielectric resin binder and an organophilic clay pigment dispersed therein; wherein the weight ratio of dielectric resin binder to organophilic clay pigment is in the range of 7:3 to 1:8; wherein the dielectric resin binder is an interpolymer containing 30 to 70 parts by weight of styrene or a substituted styrene containing 9 to 13 carbon atoms, 30 to 70 parts by weight of an acrylic ester or a methacrylic ester of a $C_1$ to $C_8$ saturated monohydric aliphatic alcohol and optionally up to 10 parts by weight of an unsaturated acid monomer selected from the group consisting of acrylic acid, methacrylic acid, crotonic acid and maleic acid, the relative viscosity of the interpolymer being in the range of from 1.1 to 3.0, measured on a 2 percent solution in benzene; and wherein the organophilic clay pigment is the reaction product of calcined kaolin clay of particle size in the range of 0.1 to 20 micron, containing from 0.1 to 2 percent by weight of water and from about 0.5 to about 6 percent by weight of an organotitanium compound containing at least two hydrolyzable groups, the organotitanium compound being represented by the formula:

$$Ti(OR)_m R'_{4-m}$$

wherein R is a hydrocarbon radical containing from 1 to 12 carbon atoms and R' is OCOR'', OR''', or OSiR'', wherein R'' is a substituted or unsubstituted hydrocarbon radical having from 1 to 40 carbon atoms and wherein R''' is a substituted or unsubstituted hydrocarbon radical having from 6 to 40 carbon atoms providing that R''' and R are not identical and wherein m is an integer of 2 or 3.

9. The dielectric recording medium of claim 8 wherein R is a hydrocarbon radical containing 1 to 8 carbon atoms and R' is a carboxyl group containing 1 to 40 carbon atoms.

10. The dielectric recording medium of claim 8 wherein the weight ratio of dielectric resin binder to organophilic clay pigment is in the range of 4.5:5.5 to 2.5:7.5.

11. The dielectric recording medium of claim 8 wherein the electroconductive substrate is a paper sheet with basis weight in the range of 15 to 100 pounds per 3000 sq. ft. and a surface resistivity less than $1 \times 10^9$ ohms per square at 50 percent relative humidity.

12. The dielectric recording medium of claim 8 wherein the thickness of the dielectric coating is in the range of 0.03 to 1.0 mil.

13. A dielectric recording medium which comprises an electroconductive substrate coated on at least one surface with a dielectric coating of thickness in the range of from 0.03 to 5 mil, said coating comprising a dielectric resin binder and an organophilic clay pigment dispersed therein; wherein the organophilic clay pigment is the reaction product of calcined clay of particle size in the range of 0.1 to 20 micron containing from 0.1 to 2 percent by weight of water and from about 0.5 to about 6 percent by weight of an organotitanium compound selected from the group consisting of trialkyl monooleyl titanate and dialkyl dioleyl titanate, wherein the alkyl group contains 1 to 8 carbon atoms; wherein the dielectric resin is an interpolymer containing 30 to 70 parts by weight of styrene or a substituted styrene containing 9 to 13 carbon atoms, 30 to 70 parts by weight of an acrylic ester or a methacrylic ester of a $C_1$ to $C_8$ saturated monohydric aliphatic alcohol and optionally up to 10 parts by weight of an unsaturated acid monomer selected from the group consisting of acrylic acid, methacrylic acid, crotonic acid and maleic acid, the relative viscosity of the interpolymer being in the range of from 1.1 to 3.0, measured on a 2 percent solution in benzene; wherein the weight ratio of dielectric resin binder to organophilic clay pigment is in the range of 7:3 to 1:8.

* * * * *

UNITED STATES PATENT OFFICE
CERTIFICATE OF CORRECTION

PATENT NO. : 3,991,253

DATED : November 9, 1976

INVENTOR(S) : Albert H. Markhart and David R. Cahill

It is certified that error appears in the above-identified patent and that said Letters Patent are hereby corrected as shown below:

At column 4, line 13, after "ester", insert --- such ---.

Signed and Sealed this

Twenty-second Day of February 1977

[SEAL]

Attest:

RUTH C. MASON
*Attesting Officer*

C. MARSHALL DANN
*Commissioner of Patents and Trademarks*